United States Patent
Donno et al.

(10) Patent No.: US 6,595,993 B2
(45) Date of Patent: Jul. 22, 2003

(54) CONNECTION OF A BONE SCREW TO A BONE PLATE

(75) Inventors: Cosimo Donno, Winterthur (CH); Simon Casutt, Gossau (CH)

(73) Assignee: Suler Orthopedics Ltd., Baar (CH)

( * ) Notice: Subject to any disclaimer, the term of this patent is extended or adjusted under 35 U.S.C. 154(b) by 30 days.

(21) Appl. No.: 09/854,227

(22) Filed: May 11, 2001

(65) Prior Publication Data

US 2001/0047174 A1 Nov. 29, 2001

(30) Foreign Application Priority Data

May 12, 2000 (EP) ............................................. 00810406

(51) Int. Cl.[7] .............................................. A61B 17/56
(52) U.S. Cl. .............................. 606/71; 606/61; 606/69
(58) Field of Search .............................. 606/61, 69, 73, 606/71

(56) References Cited

U.S. PATENT DOCUMENTS 5,372,598 A * 12/1994 Luhr et al. ..................... 606/69
6,022,350 A * 2/2000 Ganem ........................... 606/61
6,293,949 B1 * 9/2001 Justis et al. .................... 606/61

FOREIGN PATENT DOCUMENTS

| DE | 19542116 A1 | | 5/1997 | |
| EP | 0988833 A2 | | 3/2000 | |
| FR | 2778088 | | 11/1999 | |
| WO | WO 00/003653 | * | 7/1999 | ........... A61B/17/86 |
| WO | WO 00/03653 | | 1/2000 | |

* cited by examiner

Primary Examiner—Brian L. Casler
Assistant Examiner—Lina R Kontos
(74) Attorney, Agent, or Firm—Townsend and Townsend and Crew LLP

(57) ABSTRACT

With the invention the connection of a bone screw (12) to a bone plate (7) is shown. The head (13) of the bone screw (12) lies with a ring-shaped outer surface (10) in contact on a counter-surface (25) and can be fixed with a securing screw (15) which can be screwed in in the direction towards the counter-surface (25). In this the height (16) of the bone plate (7) is chosen such that it is less than or equal to the shaft diameter (19) of the bone screw (12), whereas the screw head (13) dips into a cut-out (20) of the securing screw (15) and the upper side of the securing screw (15) terminates with the upper side of the bone plate (7).

11 Claims, 4 Drawing Sheets

CONNECTION OF A BONE SCREW TO A BONE PLATE

BACKGROUND OF THE INVENTION

The invention relates to a connection of a bone screw to a bone plate, the bone screw having a head which lies with a ring-shaped outer surface in contact on a counter-surface of the bone plate and can be fixed with a securing screw which can be screwed into the bone plate in the direction towards the counter-surface, with the bone plate having a passage opening for a shaft of the bone screw.

A problem with these applications consists in that a bone screw which has once been set should form with its head a connection to the implant which is resistant to bending and which is independent of the anchoring forces between the bone screw and the bone. Thus EP-A-0 988 833 shows a connection which is resistant to bending between a bone screw with a spherical head and a bone plate. A further problem for a connection of this kind consists in that it requires a constructional height which cannot be readily reduced. In fields of application such as for example in cervical vertebrae, thin bone plates which are only insubstantially thicker in the region of the connection are advantageous.

SUMMARY OF THE INVENTION

It is an object of the invention to improve this situation. This object is satisfied in that the height of the bone plate is less than or equal to the diameter of the shaft in the region of the bone screw; in that the screw head dips into a cut-out of the securing screw; and in that the securing screw terminates with the upper side of the bone plate.

A design of the connection of this kind, which permits constructional heights which correspond at most to the shaft diameter of the bone screw, and which nevertheless results in a rigid connection which is resistant to bending, causes neither unnecessarily thick bone plates nor additionally projecting edges or surfaces which produce pressure points between the implant and the epidermis for the wearer of the implant.

The construction permits providing significantly more than half of the constructional height for the threaded length of the securing screw in spite of the low constructional height of the connection. With a design of the head of the bone screw as a spherical pan and suitable projections and recesses at the securing screw the spherical pan can be pivoted in cut-outs which lie behind the thread of the securing screw. Suitable cut-outs are for example possible when the thread diameter of the securing screw is twice as large as the shaft diameter of the bone screw. This encounters a non-pivotal bone screw which can be anchored in the direction of the axis of the securing screw as well as a pivotal bone screw which is designed with a spherical pan. If the latter with its spherical pan has outer surfaces and inner surfaces with the same sphere center, pivotings from a middle position by angles $\alpha_1$, $\alpha_2$ can be carried out which can amount to up to about 20° in order then to fix the bone screw with a securing screw. This kind of design has the advantage that the fixing of the bone plate can take place largely independently of the angular position of the bone screw. In this the bone plate is not restricted only to the connection of fragments of bone fractures, but can also be a support construction between two vertebrae.

In a use of a bone plate between two vertebrae the bridging over part can be rigid or also formed as a bending spring in order to transmit forces from one vertebra to the other vertebra.

There is also the possibility of designing at two vertebrae in each case a bone plate as anchoring body in the form of a yoke with a plurality of bone screws and to use an elastic band with an elastic pressure body as the actual support construction, as is shown in EP-B-0 669 109.

Bone screws with a shaft diameter of from 2 to 10 mm are suitable as bone screws for the anchoring.

In the following the invention will be described with reference to exemplary embodiments.

DESCRIPTION OF THE PREFERRED EMBODIMENTS

DESCRIPTION OF THE PREFERRED EMBODIMENTS

Figure 1:
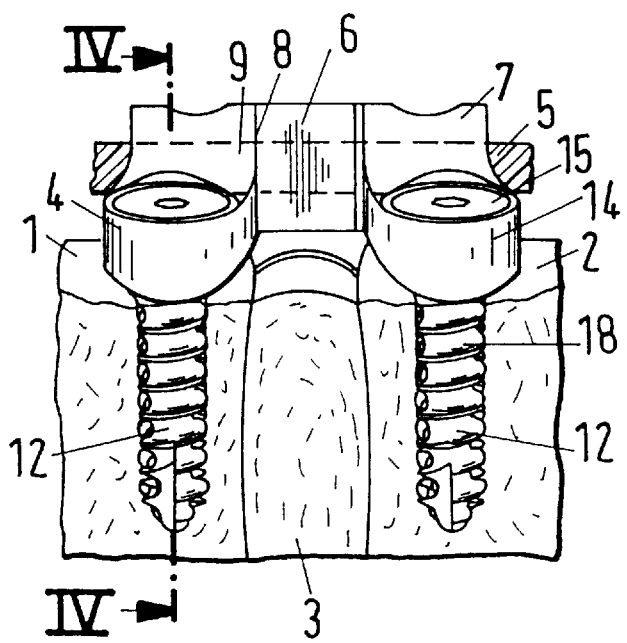
FIG. 1 shows two adjacent vertebrae at which in each case a bone plate which is designed as a yoke is anchored with bone screws, and an elastic band with an elastic pressure body acts as a connection of the two bone plates.
Figure 3:
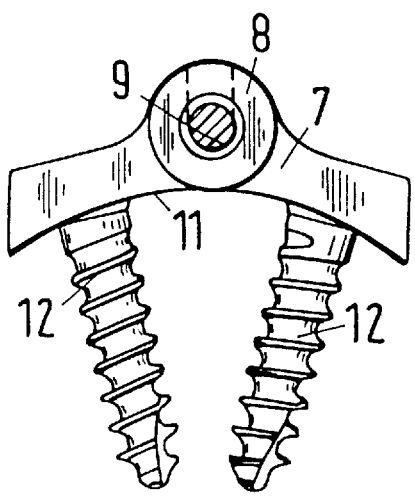
FIG. 3 is a side view of FIG. 1.
Figure 2:
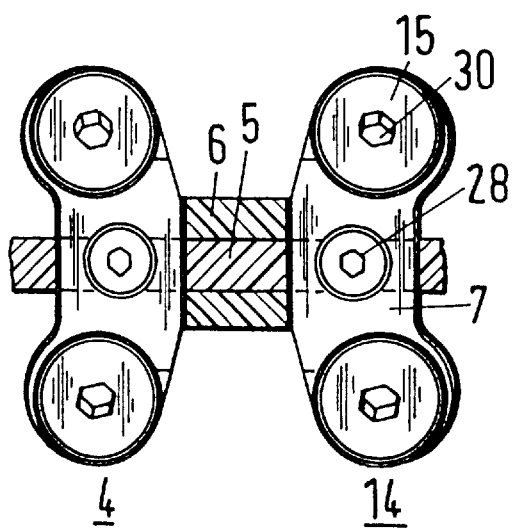
FIG. 2 is a plan view of FIG. 1.

In the figures the connection of a bone screw 12 to a bone plate 7 is shown. The head 13 of the bone screw 12 lies with a ring-shaped outer surface 10 on a counter-surface and can be fixed with a securing screw 15 which can be screwed in in the direction towards the counter-surface. In this the height 16 of the bone plate 7 is chosen such that it is less than or equal to the shaft diameter 19 of the bone screw 12, whereas the screw head 13 dips into a cut-out 20 of the securing screw 15 and the upper side of the securing screw 15 terminates with the upper side of the bone plate 7.

Figure 5:
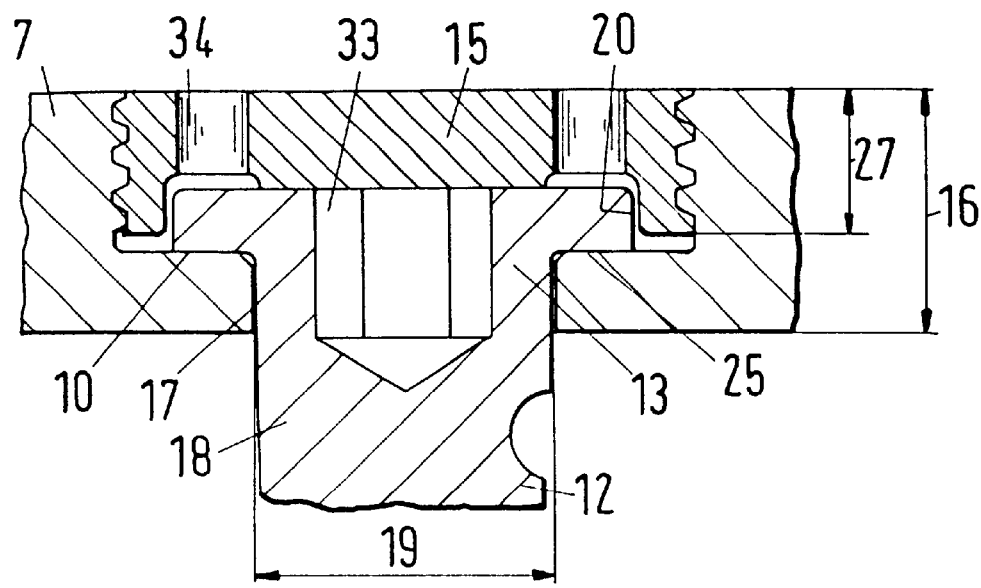
FIG. 5 shows a greatly enlarged section of the invention in which the head of the bone screw is not pivotal.

In the general example of FIG. 5 a bone screw 12 is anchored in a bone (not shown). Its head 13 has a ring-shaped outer surface 10 via which it is pressed on at a counter-surface 25 of the bone plate 7. The bone plate 7 has a passage opening 17 through which the shaft 18 of the bone screw 12 can be inserted. The screw head 13 is pressed on by a securing screw 15 in the direction of its longitudinal axis, with the head 13 dipping into a cut-out 20 of the securing screw 15 in order to save constructional height. With a thread diameter of the securing screw 15 which is greater than or equal to twice the shaft diameter 19 of the bone screw 12 the head 13 can dip in so far into the securing screw 15 that the height 16 of the bone plate 7 is less than the shaft diameter 19 and so that the threaded length 27 of the securing screw 15 amounts to more than half of the height 16. The bone screw 12 can be turned into the bone at an inner hexagon 33. The securing screw has two insertion holes 34, via which it is tightened with a tool.

Figure 6:
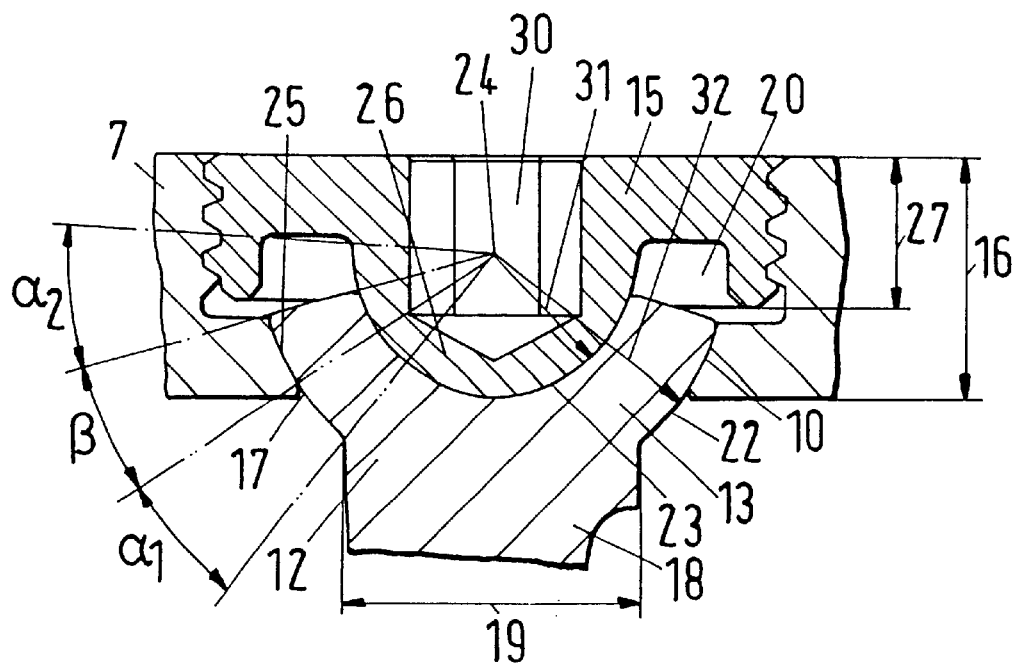
FIG. 6 shows a greatly enlarged section of the invention in which the head of the bone screw is pivotal.

In the general example of FIG. 6 the head 13 of a bone screw 12 is designed as a spherical pan with a spherical outer surface 22 and a spherical inner surface 23 which have a common center 24. The simultaneously ring-shaped 10 outer surface 22 is seated on a counter-surface 25. The ring surface 10 ends with the shaft diameter 19, which is smaller than the diameter of a passage opening 17 which is formed through the counter-surface 25. In relation to the center 24 and a middle position of the bone screw 12 the bone screw can be pivoted in any direction by a pivotal angle $\alpha_1$. In the securing screw 15 a cut-out 20 is worked in which permits a pivoting of the spherical pan by an angle $\alpha_2$, which is approximately of a magnitude equal to that of the angle $\alpha_1$. The counter-surface 25 forms an angle $\beta$ with respect to the center 24, with the angle $\beta$ being greater than the pivotal angle $\alpha_1$ in order that the outer surface 22 and the counter-surface 25 have contact in any possible angular position. A securing screw 15 protrudes with its core 26 all the way into the base of the inner surface 23 and at the same time creates space for an inner hexagon 30. The radius 31 of the inner surface 23 and the radius 32 of the outer surface 22 determine the diameters of the ring-shaped cut-out 20. The thread diameter of the securing screw 15 is chosen to be twice as large as the shaft diameter 19 in order to have sufficient material between the cut-out 20 and the thread. The threaded length 27 amounts to 60% of the height 16 of the bone plate 7. The height 16 amounts to 85% of the shaft diameter 19 of the bone screw 12. A thread is cut into the shaft 18 of the bone screw 12.

Figure 4:
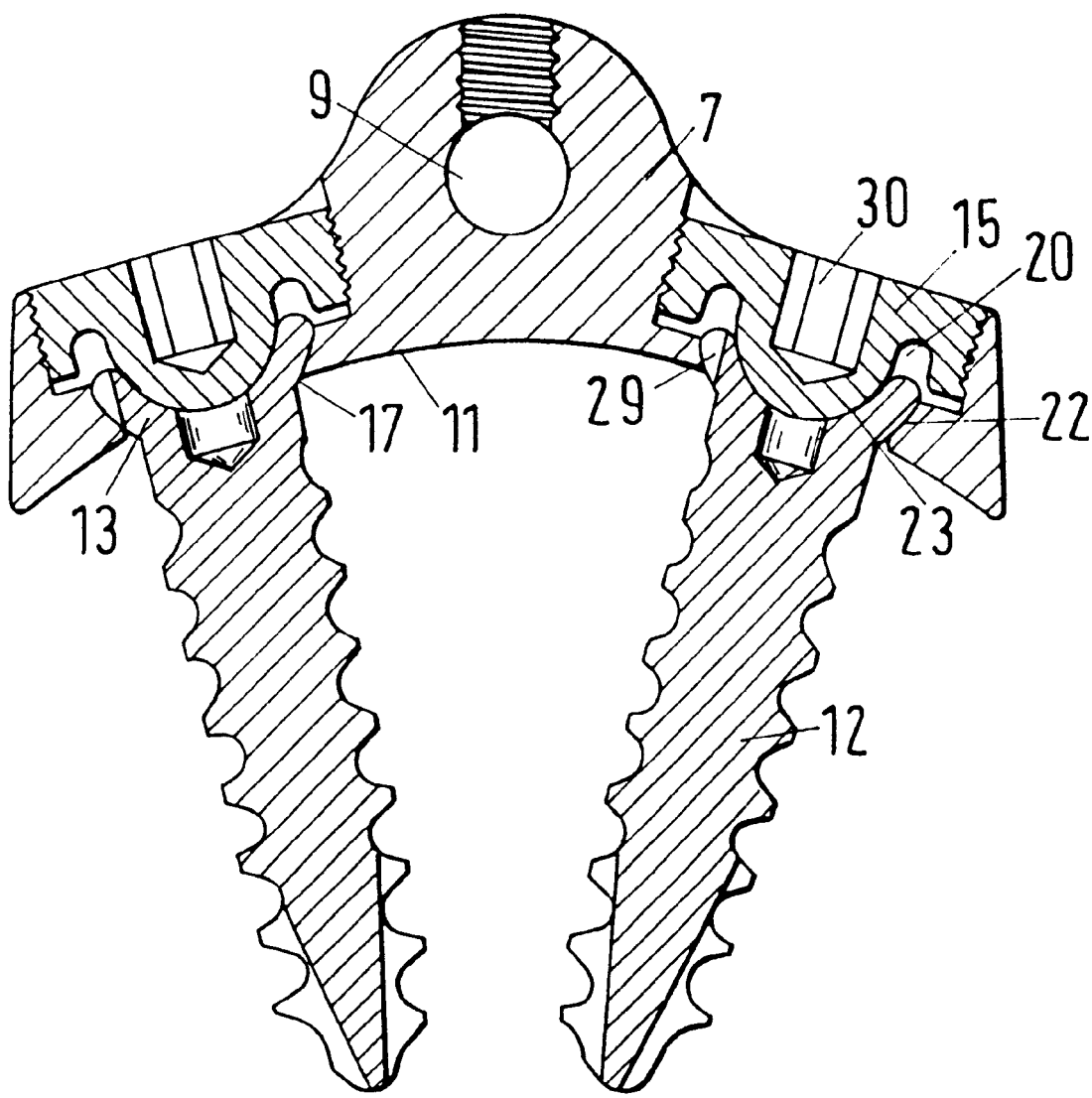
FIG. 4 is an enlarged longitudinal section of FIG. 1.

In the exemplary embodiment of FIGS. 1, 2, 3 and 4 the bone plate forms in each case a yoke with passage openings 17 at both sides, into which the head 13 of a bone screw 12 lies in contact (FIG. 4). A first bone screw 12 is inserted with its shaft through the passage opening 17 and is taken up with a screwing tool (not shown) at cut-outs 29 and turned into a prepared bore in the bone. A second bone screw is likewise turned in on the opposite side until the contact side 11 of the yoke lies in contact at the bone. Then securing screws 15 are tightened at their inner hexagon 30 with a wrench in order to produce a rigid connection between the bone screw and the yoke in the angular position of the bone screws 12 which is determined by the bone. In the present example two bone plates 7 which are secured on adjacent vertebrae 1, 2 form the basis for an elastic support construction in which an elastic pressure body 6 and an elastic draw band 5 are tensioned one against the other in order to permit limited movements between the two vertebrae 1, 2 and to relieve an intervertebral disc 3 lying between them. The draw band 5 is in each case secured with a setting screw 28 in a passage bore 9 of the yoke. The pressure body 6 lies in each case on a ring-shaped support surface 8 of the yoke.

Figure 8:
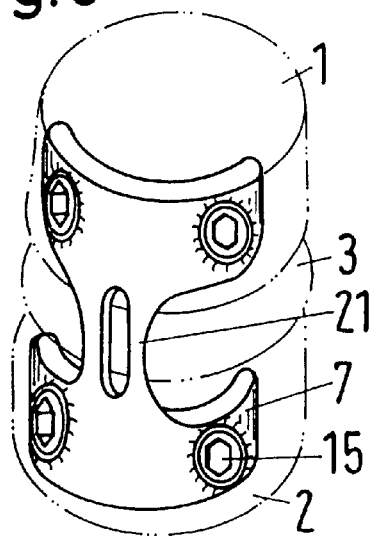
FIG. 8 shows an embodiment between two adjacent vertebrae in which the bone plate connects the two vertebrae as a bending spring.
Figure 9:
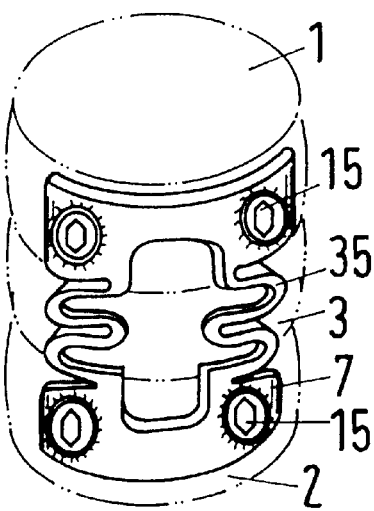
FIG. 9 shows an embodiment as in FIG. 8 with another shape of the bending spring.

Similar uses are shown by the exemplary embodiments of FIG. 8 and FIG. 9, in which the bone plates and the support construction are executed in a single piece. A bone plate 7 is in each case connected by two bone screws and via securing screws 15 to two adjacent vertebrae 1, 2 and has a bridge 21 which bridges over the distance between the two vertebrae. The bridge 21 can be more or less rigid. In the example of FIG. 9 it is designed as a double, meandering bending spring 35. Such space-saving embodiments are advantageous in the region of the cervical vertebrae.

Figure 7:
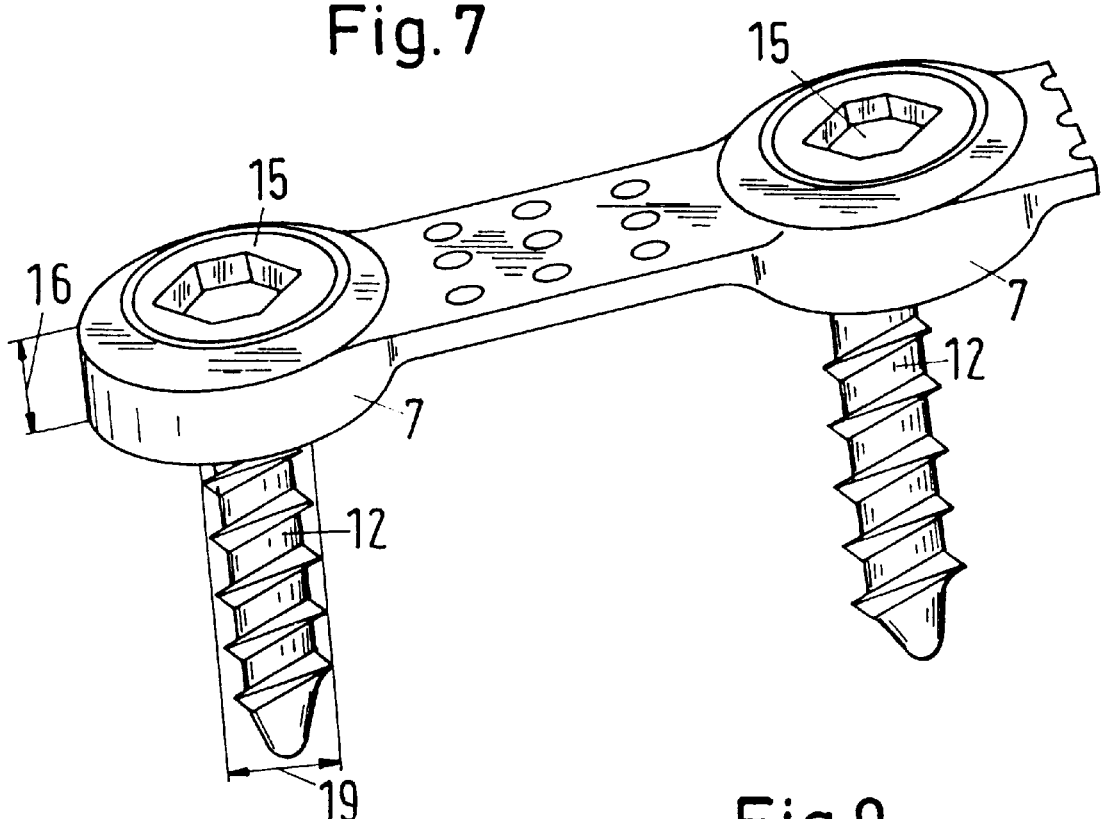
FIG. 7 shows use of the invention with a bone plate for the osteosynthesis.

A general embodiment for the osteosynthesis is shown by the example of FIG. 7. Bone screws 12 can be turned in along a bone plate 7 into different bone fragments (not shown) and rigidly connected to the bone plate 7 with securing screws 15. In the present case the bone plate is weakened between the bone screws 12 in order to permit a matching to the bone shape through bending during the operation. Again the low height 16 of the bone plate 7, which is smaller than the shaft diameter 19 of the bone screws, acts advantageously.

In principle the invention can be used for all shaft diameters of bone screws.

What is claimed is:

1. A connection comprising a bone screw for screwing into a bone and a bone plate, the bone screw including a head which lies with a ring-shaped outer surface in contact on a counter-surface of the bone plate and is fixed with a securing screw which is screwed into the bone plate in the direction towards the counter-surface, the bone plate having a passage opening for a shaft of the bone screw, a height of the bone plate in a region of the bone screw being less than or equal to a diameter of the shaft, the screw head dipping into a cut-out of the securing screw, the securing screw terminating at an upper side of the bone plate, the head of the bone screw including a spherical pan with an outer surface and an inner surface having a common center, and the securing screw dipping into the pan with a suitable core.

2. Connection in accordance with claim 1 wherein the securing screw has a threaded length which dips into the bone plate and which amounts to more than half the height of the bone plate in the region of the bone screw.

3. Connection in accordance claim 1 wherein the cut-out of the securing screw is dimensioned such that the head of the bone screw can be fixed at different angular positions with respect to the axis of the securing screw.

4. Connection in accordance with claim 3 wherein in relation to a middle position of the bone screw in the direction of the axis of the securing screw the head permits a fixing position with an angular deflection $\alpha_1$ at its outer surface; wherein the cut-out of the securing screw permits an angular deflection $\alpha_2$ of similar magnitude for the screw head; and wherein an angle $\beta$ with respect to the center which is taken up by the counter-surface is greater than the respective angle $\alpha_1$, $\alpha_2$.

5. Connection in accordance with claim 4 wherein the angles $\alpha_1$, $\alpha_2$ correspond in each case to an angle from 3° to 20°.

6. Connection in accordance with claim 1 wherein the bone plate is formed as a yoke which can be used as an anchoring body for a support construction at a vertebra.

7. Connection in accordance with claim 1 wherein the bone plate can be used as a bridge between two vertebrae.

8. Connection in accordance with claim 7, comprising a bridge which bridges over the distance between two vertebrae and is formed as a bending spring.

9. Connection in accordance with claim 1 wherein the shaft diameter of the bone screw amounts to between 2 and 10 mm.

10. A connection comprising a bone screw for screwing into a bone and a bone plate, the bone plate including a passage opening surrounded by a counter outer surface, the bone screw extending through the passage opening and having a head supported by the counter-surface of the bone plate, and a securing screw placed over the bone screw and threaded into the bone plate, the securing screw including a cut-out formed to receive at least a portion of the bone screw head so that, upon tightening the securing screw, the head of the bone screw is pressed against the ring-shaped outer surface of the bone plate, the head of the bone screw having a concave, spherically shaped inner surface facing towards the securing screw and a spherically shaped outer surface which is concentric with the inner surface and in engagement with the counter-surface, the securing screw including a spherically shaped, convex core which contacts the concave inner surface of the bone screw when the securing screw is tightened into the bone plate.

11. A connection comprising a bone screw for screwing into a bone and a bone plate, the bone plate including an opening surrounded by a counter outer surface, the bone screw extending through the opening and having a head supported by the counter-surface of the bone plate, and a securing screw placed over the bone screw and threaded into the bone plate, the securing screw including a core engaging a portion of the bone screw head so that, upon tightening the securing screw, the head of the bone screw is pressed against the ring-shaped outer surface of the bone plate, the core, the head of the bone screw and the counter-surface defining cooperating and concentric concave and convex surfaces which permit an angular adjustment of the bone screw relative to the bone plate and the securing screw.

* * * * *